(12) United States Patent
Chien et al.

(10) Patent No.: US 10,895,910 B2
(45) Date of Patent: Jan. 19, 2021

(54) ADAPTIVE EYE-TRACKING CALIBRATION METHOD

(71) Applicant: National Taiwan University, Taipei (TW)

(72) Inventors: Shao-Yi Chien, Taipei (TW); Liang Fang, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 16/299,026

(22) Filed: Mar. 11, 2019

(65) Prior Publication Data

US 2020/0183489 A1    Jun. 11, 2020

(30) Foreign Application Priority Data

Dec. 11, 2018  (TW) .............................. 107144502 A

(51) Int. Cl.
   *G06F 3/01*    (2006.01)
   *A61B 3/113*   (2006.01)
   *G06K 9/00*    (2006.01)

(52) U.S. Cl.
   CPC .............. *G06F 3/013* (2013.01); *A61B 3/113* (2013.01); *G06K 9/00604* (2013.01)

(58) Field of Classification Search
   CPC ..... G06K 3/013; G06K 9/00604; A61B 3/113
   See application file for complete search history.

(56) References Cited

U.S. PATENT DOCUMENTS

| | | | |
|---|---|---|---|
| 2016/0011658 A1* | 1/2016 | Lopez | G06K 9/00597 345/156 |
| 2018/0335839 A1* | 11/2018 | Lin | G06K 9/3233 |
| 2019/0354172 A1* | 11/2019 | Davies | G06F 3/013 |

FOREIGN PATENT DOCUMENTS

CN    108960045 A    12/2018

OTHER PUBLICATIONS

Office Action dated May 23, 2019 in corresponding Taiwan Patent Application No. 107144502.

* cited by examiner

*Primary Examiner* — Maria E Vazquez Colon
(74) *Attorney, Agent, or Firm* — Donald E. Stout; Stout, Uxa & Buyan, LLP

(57) ABSTRACT

An adaptive eye-tracking calibration method includes generating an eye model acting as a current eye model; calibrating the eye model; comparing real-time pupil data set and pupil data set of the current eye model to obtain a pupil data difference when an event happens; and generating a new eye model if the pupil data difference is greater than a predetermined threshold.

14 Claims, 3 Drawing Sheets

ADAPTIVE EYE-TRACKING CALIBRATION METHOD

CROSS-REFERENCE TO RELATED APPLICATIONS

This application claims priority of Taiwan Patent Application No. 107144502, filed on Dec. 11, 2018, the entire contents of which are herein expressly incorporated by reference.

BACKGROUND OF THE INVENTION

1. Field of the Invention

The present invention generally relates to eye tracking, and more particularly to an adaptive eye-tracking calibration method.

2. Description of Related Art

Eye tracking is a technique of measuring the gaze position of eyes by using sensors. Eye-tracking devices (or eye trackers) may be classified into remote type and mobile type according to their configuration. As distance between a remote eye-tracking device and eyes is at least tens of centimeters, the remote eye-tracking device possesses low accuracy. A mobile eye-tracking device is disposed near eyes (e.g., disposed at glasses) and thus has high accuracy. There are limits on usage time (e.g., a couple of hours) of the eye-tracking device as power source needs be continuously turned on while performing tracking.

The eye-tracking device may be adaptable to a variety of applications such as healthcare for preventing dry eye syndrome by detecting eye blinking. The eye-tracking device may be adaptable to driving safety for preventing fatigue driving by analyzing driving concentration. The eye-tracking device may be adaptable to virtual reality (VR) or augmented reality (AR) for achieving better performance by collecting auxiliary information.

A calibration procedure is commonly performed before using the eye-tracking device. FIG. 1 shows a schematic diagram illustrating conventional eye-tracking calibration. In the conventional eye-tracking calibration procedure, an eye model and an optical axis are obtained by detecting the position of a reflection point, and a visual axis is obtained based on calibration points. Finally, the difference between the optical axis and the visual axis is computed to accomplish the calibration.

The conventional eye-tracking devices may inevitably suffer displacement or slide during operation or when being used again after operation, thereby causing inaccuracy or error. A need has thus arisen to propose a novel eye-tracking calibration method to improve on the conventional eye-tracking devices.

SUMMARY OF THE INVENTION

In view of the foregoing, it is an object of the embodiment of the present invention to provide an adaptive eye-tracking calibration method adaptable to an eye-tracking device for obtaining a gaze position of eyes. The embodiment is capable of adaptively performing automatic compensation or calibration to prevent the eye-tracking device from inaccuracy or error when displacement of the eye-tracking device occurs.

According to one embodiment, the adaptive eye-tracking calibration method may include the following steps: (a) generating an eye model acting as a current eye model; (b) calibrating the eye model; (c) comparing real-time pupil data set and pupil data set of the current eye model to obtain a pupil data difference when a predetermined event happens; and (d) generating a new eye model if the pupil data difference is greater than a predetermined threshold.

DETAILED DESCRIPTION OF THE INVENTION

Figure 1:
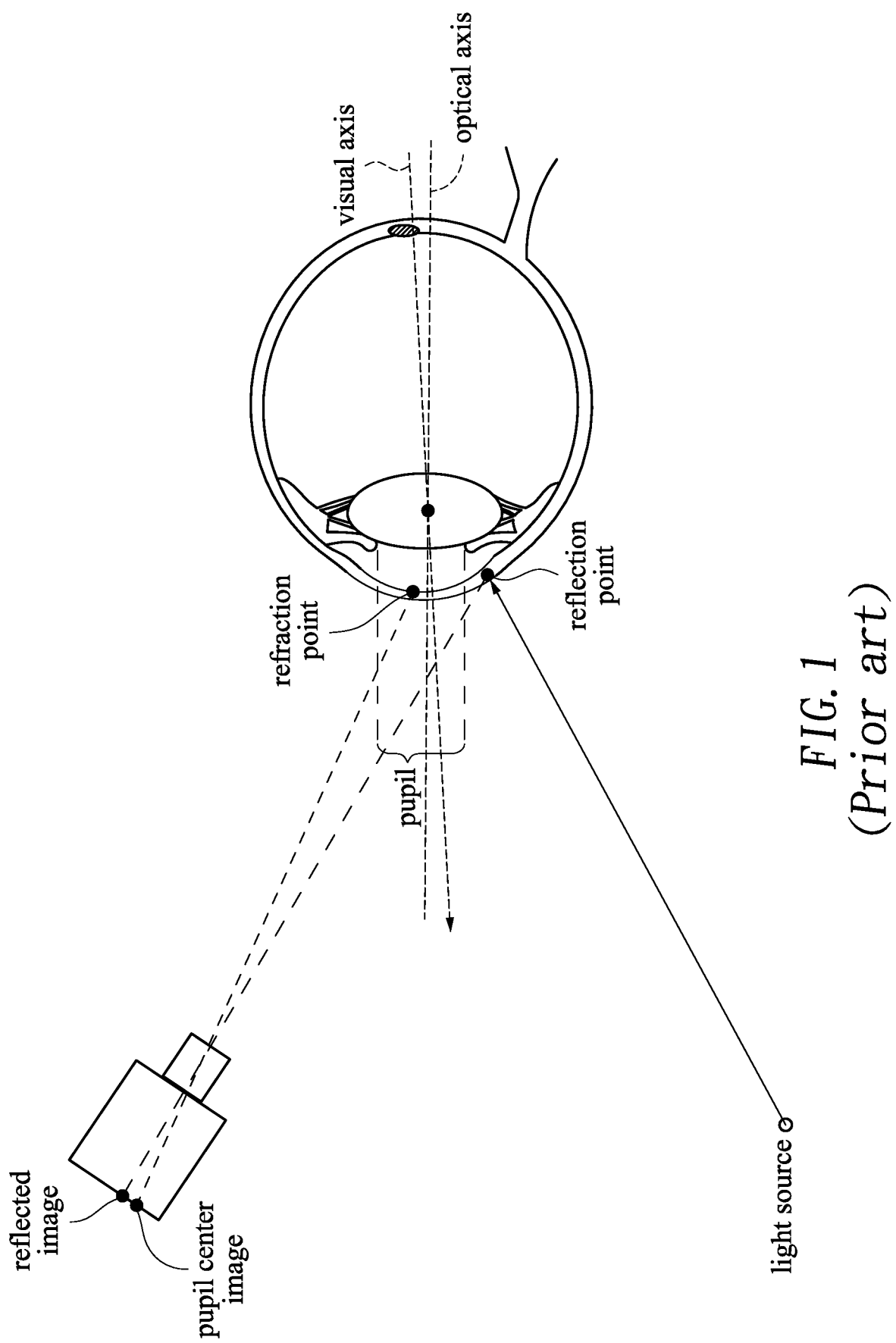
FIG. 1 shows a schematic diagram illustrating conventional eye-tracking calibration.
Figure 2:
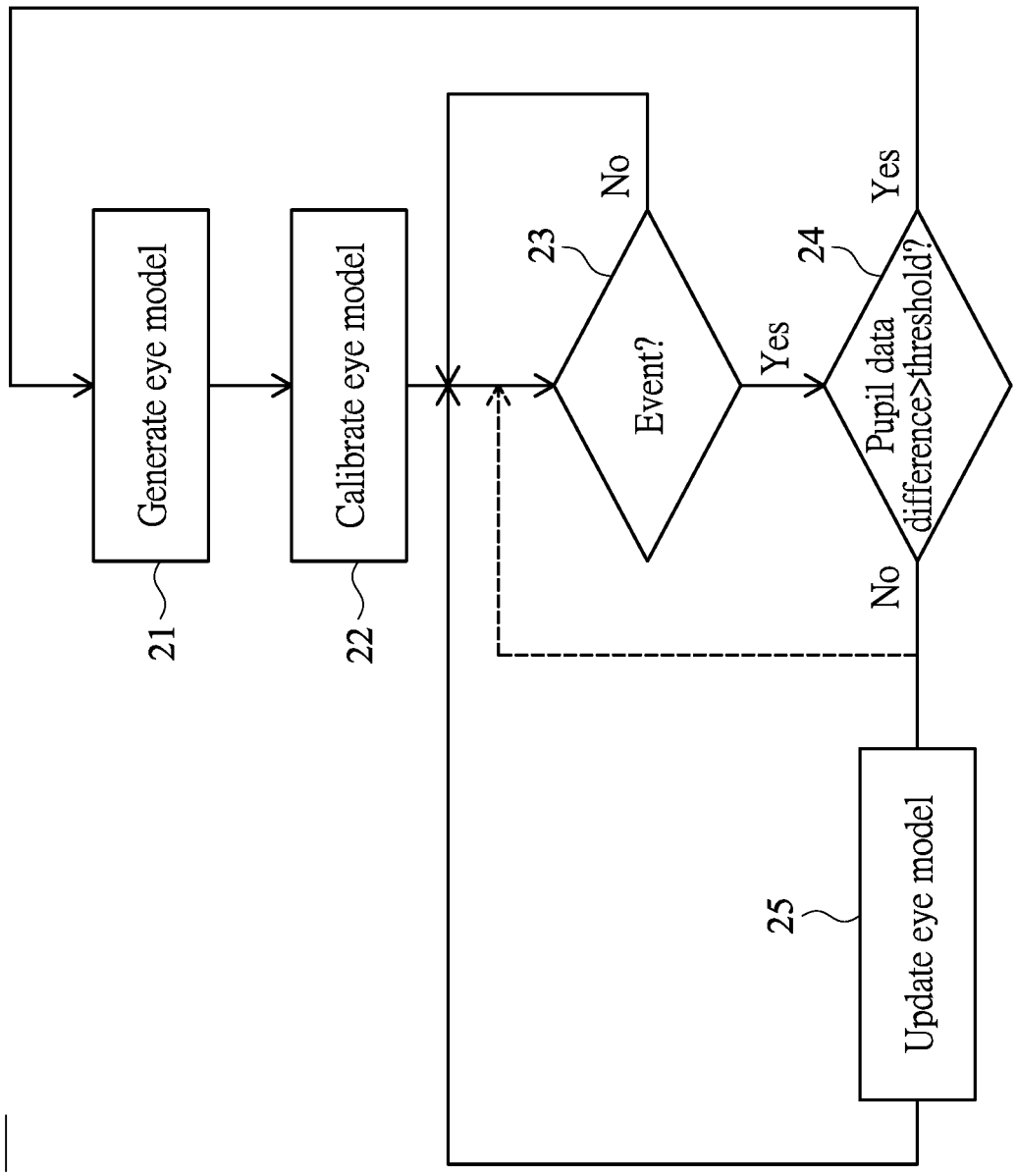
FIG. 2 shows a flow diagram illustrating an adaptive eye-tracking calibration method according to one embodiment of the present invention.
Figure 3:
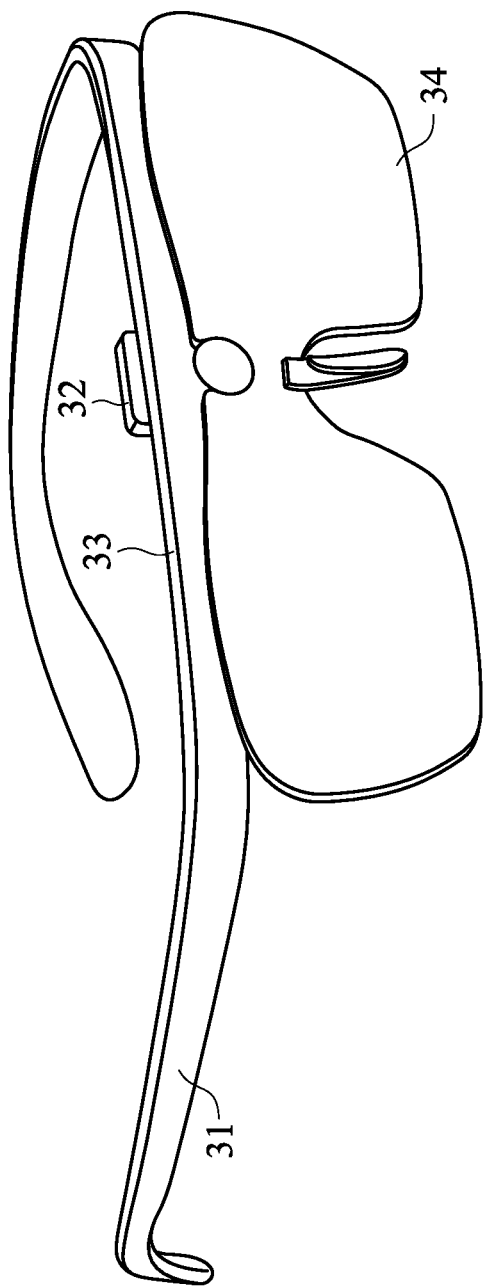
FIG. 3 shows a perspective view of exemplary smart glasses.

FIG. 2 shows a flow diagram illustrating an adaptive eye-tracking calibration method (calibration method hereinafter) 200 adaptable to automatically calibrating an eye-tracking device to obtain a gaze position of eyes according to one embodiment of the present invention. The embodiment may be adaptable to a remote eye-tracking device, which, for example, is 0.5 meter away from the eyes. The embodiment may be adaptable to a mobile eye-tracking device such as wearable computer glasses or smart glasses. FIG. 3 shows a perspective view of exemplary smart glasses, which may primarily include legs 31, a frame 33 and lenses 34. The smart glasses may also include a control box 32 disposed at the frame 33 or the legs 31. The control box 32 may include a processor (e.g., digital image processor) configured to perform the calibration method 200 of the embodiment. The control box 32 may also include other eye-tracking components such as sensor or illuminator.

In the embodiment as shown in FIG. 2, in step 21, pupil images are collected to obtain corresponding pupil data set, according to which an eye model may be generated to act as a current eye model. An optical axis representing a pupil vector may be obtained according to the generated eye model. In the embodiment, the eye model may be generated using a conventional method, details of which are omitted for brevity.

Next, in step 22, a visual axis may be obtained based on at least one calibration point. The eye model (generated in step 21) may be calibrated according to a difference between the visual axis and the optical axis. Specifically, in the embodiment, a rotation matrix is computed based on the calibration point and the optical axis, and the difference between the visual axis and the optical axis is then compensated by rotation matching based on the rotation matrix, thereby accomplishing calibration.

After the calibration, the eye-tracking device may proceed to perform eye tracking. However, the eye-tracking device (e.g., smart glasses) may inevitably suffer displacement or slide during operation or when being used again after operation. In view of that, the following steps of the embodiment may adaptively perform automatic compensation or calibration to prevent the eye-tracking device from inaccuracy or error.

In step 23, it is determined whether a predetermined event happens. In one embodiment, a timer is used to determine whether a predetermined time interval elapses. When the predetermined time interval elapses (indicating that the predetermined event happens), the flow goes to step 24; otherwise step 23 repeats itself. Accordingly, the embodiment may adaptively perform automatic compensation or calibration in the following steps at intervals. In the specification, the predetermined event may be set in a system boot or may be dynamically set during system operation.

In an alternative embodiment, one or more event sources may be waited for in step 23. When the event source triggers or notifies the predetermined event, the flow goes to step 24; otherwise step 23 repeats itself. Accordingly, the embodiment may adaptively perform automatic compensation or calibration in the following steps when needed.

In step 24, (when the predetermined event happens,) real-time pupil images are collected to obtain corresponding real-time pupil data set, which is compared with pupil data set of the current eye model to obtain an (absolute) pupil data difference therebetween. If the pupil data difference is greater than a predetermined threshold (indicating that the pupil data set of the current eye model possesses substantive error, or geometric distance between a center of the current eye model and the corresponding optical axis is very great and distribution of the pupil data set is overly dispersive), the flow goes to step 21 to generate a new eye model acting as a current eye model. As stated above, the predetermined time interval in step 23 may be dynamically set. For example, the greater the pupil data difference is, the smaller the predetermined time interval is set. Therefore, the calibration method 200 of the embodiment may be performed more frequently. To the contrary, the smaller the pupil data difference is, the greater the predetermined time interval is set. Therefore, the calibration method 200 of the embodiment may be performed less frequently.

If the pupil data difference is not greater than the predetermined threshold (indicating that the pupil data set of the current eye model possesses no substantive error), the flow goes to step 25 to update the current eye model according to the real-time pupil data set (obtained in step 24).

In an alternative embodiment, if the pupil data difference is not greater than the predetermined threshold, for example, the pupil data difference is too small (e.g., substantially smaller than the predetermined threshold), the flow goes back to step 23 without performing step 25 as denoted by the dashed line.

According to the embodiment as set forth above, as the eye-tracking device may suffer displacement during operation or when being used again after operation, the embodiment may adaptively perform automatic compensation or calibration without user intervention and use interruption.

Although specific embodiments have been illustrated and described, it will be appreciated by those skilled in the art that various modifications may be made without departing from the scope of the present invention, which is intended to be limited solely by the appended claims.

What is claimed is:

1. An adaptive eye-tracking calibration method, comprising:
   (a) generating an eye model acting as a current eye model;
   (b) calibrating the eye model;
   (c) detecting whether at least an event happens, wherein the event includes that a predetermined time interval elapses;
   (d) comparing real-time pupil data set and pupil data set of the current eye model to obtain a pupil data difference when the event happens, otherwise repeating step (c); and
   (e) generating a new eye model if the pupil data difference is greater than a predetermined threshold, otherwise updating the current eye model according to the real-time pupil data set if the pupil data difference is not greater than the predetermined threshold.

2. The method of claim 1, wherein the step (a) comprises:
   collecting a plurality of pupil images to obtain corresponding pupil data set, according to which the eye model is generated; and
   obtaining an optical axis according to the generated eye model.

3. The method of claim 2, wherein the step (b) comprises:
   obtaining a visual axis based on at least one calibration point; and
   calibrating the eye model according to a difference between the visual axis and the optical axis.

4. The method of claim 3, wherein the step (b) comprises:
   computing a rotation matrix based on the calibration point and the optical axis, and compensating the difference between the visual axis and the optical axis by rotation matching based on the rotation matrix, thereby calibrating the eye model.

5. The method of claim 1, wherein the event is determined by using a timer to determine whether the predetermined time interval elapses, and the event happens when the predetermined time interval elapses.

6. The method of claim 5, wherein the predetermined time interval is dynamically set according to the pupil data difference.

7. The method of claim 1, wherein the event is determined by waiting for one or more event sources, and the event happens when the event source triggers or notifies the event.

8. The method of claim 1, further comprising:
   determining whether the event happens if the pupil data difference is not greater than the predetermined threshold.

9. An adaptive eye-tracking calibration method, comprising:
   (a) collecting a plurality of pupil images to obtain corresponding pupil data set, according to which an eye model is generated to act as a current eye model;
   (b) obtaining an optical axis according to the eye model;
   (c) obtaining a visual axis based on at least one calibration point;
   (d) calibrating the eye model according to a difference between the visual axis and the optical axis;
   (e) determining whether at least an event happens, wherein the event includes that a predetermined time interval elapses;
   (f) comparing real-time pupil data set and pupil data set of the current eye model to obtain a pupil data difference when the event happens, otherwise repeating step (e); and
   (g) generating a new eye model if the pupil data difference is greater than a predetermined threshold, otherwise updating the current eye model according to the real-time pupil data set if the pupil data difference is not greater than the predetermined threshold.

10. The method of claim 9, wherein the step (d) comprises:
    computing a rotation matrix based on the calibration point and the optical axis, and compensating the difference between the visual axis and the optical axis by rotation matching based on the rotation matrix, thereby calibrating the eye model.

11. The method of claim 9, wherein the step (e) comprises:

using a timer to determine whether the predetermined time interval elapses, wherein the event happens when the predetermined time interval elapses.

12. The method of claim 11, wherein the predetermined time interval is dynamically set according to the pupil data difference.

13. The method of claim 9, wherein the step (e) comprises:
waiting for one or more event sources, wherein the event happens when the event source triggers or notifies the event.

14. The method of claim 9, further comprising:
performing the step (e) to determine whether the event happens if the pupil data difference is not greater than the predetermined threshold.

* * * * *